(12) United States Patent
Korlach et al.

(10) Patent No.: US 7,563,574 B2
(45) Date of Patent: Jul. 21, 2009

(54) METHODS, SYSTEMS AND COMPOSITIONS FOR MONITORING ENZYME ACTIVITY AND APPLICATIONS THEREOF

(75) Inventors: Jonas Korlach, Menlo Park, CA (US); Stephen Turner, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 11/394,637

(22) Filed: Mar. 31, 2006

(65) Prior Publication Data

US 2007/0231804 A1 Oct. 4, 2007

(51) Int. Cl.
*C12Q 1/68* (2006.01)
*C12Q 1/66* (2006.01)
*C12Q 1/48* (2006.01)

(52) U.S. Cl. .................. 435/6; 435/8; 435/15
(58) Field of Classification Search ........................ None
See application file for complete search history.

(56) References Cited

U.S. PATENT DOCUMENTS

| | | | |
|---|---|---|---|
| 5,547,839 | A | 8/1996 | Dower et al. |
| 5,821,058 | A | 10/1998 | Smith et al. |
| 6,210,896 | B1 | 4/2001 | Chan |
| 6,818,395 | B1 | 11/2004 | Quake et al. |
| 6,869,764 | B2 | 3/2005 | Williams et al. |
| 6,982,146 | B1 | 1/2006 | Schneider et al. |
| 7,033,762 | B2 | 4/2006 | Nelson et al. |
| 7,033,764 | B2 | 4/2006 | Korlach et al. |
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,064,197 | B1 | 6/2006 | Rabbani et al. |
| 2002/0039738 | A1 * | 4/2002 | Williams et al. ............. 435/6 |
| 2003/0186276 | A1 | 10/2003 | Odera |
| 2003/0190647 | A1 | 10/2003 | Odera |
| 2003/0194740 | A1 | 10/2003 | Williams |
| 2003/0215862 | A1 | 11/2003 | Parce et al. |
| 2004/0048301 | A1 | 3/2004 | Sood et al. |
| 2004/0224319 | A1 | 11/2004 | Sood et al. |
| 2006/0051807 | A1 * | 3/2006 | Fuller ............................. 435/6 |

FOREIGN PATENT DOCUMENTS

| | | |
|---|---|---|
| EP | 1105529 B1 | 11/2005 |
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO 01/16375 A2 | 3/2001 |
| WO | WO 2004072304 A1 * | 8/2004 |

OTHER PUBLICATIONS

Nyren et al. Enzymatic method for continuous monitoring of DNA polymerase activity. Analytical Biochemistry (1987) 167: 235-238.*
Satoh et al. ATP amplification for ultrasensitive bioluminescence assay: detection of a single bacterial cell. Bioscience, Biotechnology, and Biochemistry (2004) 68(6): 1216-1220.*
Ronaghi et al. A Sequencing Method Based on Real-Time Pyrophosphate. Science (1998) 281(5375): 363 & 365.*
M. J. Levene, et al., "Zero-Mode Waveguides for Single-Molecule Analysis at High Concentrations," *Science*, 299:682-686 (Jan. 31, 2003).

* cited by examiner

*Primary Examiner*—Kenneth R. Horlick
*Assistant Examiner*—Angela Bertagna
(74) *Attorney, Agent, or Firm*—Matthew B. Murphy

(57) ABSTRACT

Methods of monitoring enzyme mediated reactions, and particularly nucleic acid synthesis reactions such as pyrosequencing methods that employ enzymatic reporter systems. The methods and systems provide elevated signal levels as compared to conventional pyrosequencing processes, and/or mediate de-phasing of sequencing analyses employing pyrosequencing or other "sequencing by synthesis" methods.

9 Claims, 2 Drawing Sheets

METHODS, SYSTEMS AND COMPOSITIONS FOR MONITORING ENZYME ACTIVITY AND APPLICATIONS THEREOF

CROSS-REFERENCE TO RELATED APPLICATIONS

Not applicable.

STATEMENT REGARDING FEDERALLY SPONSORED RESEARCH

Not applicable.

BACKGROUND OF THE INVENTION

Biological and biochemical analyses routinely monitor biological functions by utilizing model systems and/or measuring a proxy for naturally occurring products and/or reactants of those biological processes. For example, a wide range of such analyses use model substrates for such systems that include detectable labels so that one can readily identify and even quantitate the functioning of the system, e.g., through the determination of the amount of substrate used and/or product produced from a given system. Such labeled materials may include fluorescent or fluorogenic labeling groups, chromophoric or chromogenic labeling groups, or luminescent labeling groups.

In many cases, the materials and model systems are selected to provide a signaling event that is the direct result of the operation of the biological system being analyzed. For example, such systems may include substrates that provide a fluorescent signal change when acted upon by a given enzyme or other system that is to be analyzed. Such changes may include the creation, increase, decrease or changed character of the fluorescent signal as a result of the action of the system. By directly measuring the change in signal as a result of the action of the system, one can monitor and even quantify the functioning of the system.

In a number of cases, direct signaling systems may not be available. In some cases, this may result from the lack of availability of model systems that provide such direct systems, e.g., no fluorogenic substrates are available, or substrate and product are not sufficiently different to create a meaningful fluorescent or other signal. As a result, analyses have been used that rely upon other avenues for detection. For example, kinase analyses have long suffered from a lack of fluorogenic assay systems. As a result, assay systems have been developed that are based upon a shift in charge between the non-phosphorylated substrate and the phosphorylated product. Such systems range from electrophoretic separations of substrate and product (See, U.S. Pat. No. 6,274,089), antibody based binding assays (See, e.g., PanVera Corp, Phosphotyrosine Assay Kit # P2836 and 2837), and fluorescence polarization based assay methods (See, U.S. Pat. No. 6,287,774) for measuring changes in the level of phosphorylated product in the system.

In still other cases, cascades or collections of interacting systems have been used to provide a signal mechanism for systems that lack a convenient direct signaling system. In such systems, a separate system is fed by the product or substrate of the system of interest to yield or signal that is related to the generation of product or consumption of substrate, or the like. Such systems are generally referred to as "reporter systems".

The field of nucleic acid sequencing has suffered from a lack of reagent systems that provide a convenient readout of sequence information. Instead, sequencing has relied upon complex reaction mixtures that produce nested sets of sequence fragments that are then separated by size and identified by their labeled dideoxynucleotide terminator, e.g., to identify the base by which each fragment was extended over it's preceding fragment. Sequencing by synthesis systems, e.g., which monitor the stepwise addition of nucleotides in a synthesizing nucleotide strand have similarly lacked convenient direct detection systems in the past. In particular, being able to detect each added base and then proceed to add and detect additional bases has proven difficult.

A number of potential approaches have been proposed and/or developed in this area to deal with some of these shortcomings. Notwithstanding such improvements, additional improvements to such systems are desirable. The present invention meets these and a variety of other needs.

BRIEF SUMMARY OF THE INVENTION

The present invention is generally directed to improved assay systems and particularly to improved assay systems that monitor the activity of enzymes capable of producing pyrophosphate from nucleoside polyphosphates. The methods of the present invention employ improved substrates that provide enhanced detection of the product of the reaction that is being monitored, either through direct detection or first conversion into detectable species which are then detected.

The present invention, in at least one aspect, provides a methods of monitoring activity of an enzyme that is capable of producing pyrophosphate from a nucleoside triphosphate. The methods comprise contacting the enzyme with an unlabeled nucleoside polyphosphate having more than three phosphate groups, and detecting polyphosphate released from the nucleoside polyphosphate as an indicator of enzyme activity. Typically such detection employs a luciferase mediated detection system.

In a related aspect, the invention similarly provides methods of identifying at least a first nucleotide in a template nucleic acid. The methods comprise providing a polymerase/template primer complex, and sequentially contacting the complex with each of a plurality of different unlabeled nucleoside polyphosphates having more than three phosphate groups. The identity of a nucleoside polyphosphate that is incorporated into a nascent nucleic acid strand in a position complementary to the first nucleotide, is determined by detecting released polyphosphate.

Similarly, the invention provides methods of monitoring an activity of a polymerase enzyme in a similar fashion. In particular, the methods comprise contacting the polymerase with a nucleoside polyphosphate comprising more than three phosphate groups, wherein the polymerase releases polyphosphate group having at least three phosphates. The polyphosphate group is then converted into at least two ATP molecules for each polyphosphate group released; and the ATP produced in the converting step is detected. In certain cases the amount of ATP may be quantified to some extent, as an indication of an activity of the polymerase enzyme.

In preferred aspects, the polymerase enzyme processes the molecule to release a $P_{n-1}$ group. The $P_{n-1}$ groups are converted to more than one ATP molecule, and the more than one ATP molecules are detected as an indication of an activity of the enzyme.

In yet a further aspect, the invention provides methods of monitoring activity of an enzyme system that is capable of releasing pyrophosphate from a nucleoside triphosphate. The methods comprise contacting the enzyme system with a nucleoside polyphosphate having more than three phosphate groups, and contacting polyphosphate released from the nucleoside polyphosphate with an enzyme system capable of producing up to two or more ATP molecules from each polyphosphate molecule. The ATP produced is then detected.

In still further aspects, the invention provides improved processes of determining a nucleic acid sequence that use a separate, stepwise addition of each of four different nucleotides to a polymerization complex that includes a template sequence, a primer sequence and a polymerase enzyme, under conditions suitable for template dependent nucleic acid polymerization, and monitoring whether a nucleotide added to the polymerization complex was incorporated, to identify a sequence of nucleotides in the template sequence. The methods comprise, in a first set of nucleotide additions to the polymerization complex, separately adding each of four different nucleotides to the polymerization complex in a first order. Following such first set of additions, in a second set of nucleotide additions to the polymerization complex, a plurality of the different nucleotides from the four different nucleotides are added to the polymerization complex in a second order.

DETAILED DESCRIPTION OF THE INVENTION

I. General Description

The present invention generally provides a system and/or method for monitoring the activity of an enzyme or enzyme system that provides an amplified or enhanced signaling capability over conventional or available methods or systems for monitoring such activity. In particular, the present invention is directed to methods, compositions and kits for monitoring the activity of enzymes or enzyme systems that are generally capable of liberating phosphate groups such as pyrophosphate, from nucleoside triphosphates. In particular, the invention provides the use of nucleoside polyphosphate analogs in such assays, where such polyphosphates contain more than three phosphates in the polyphosphate chain, and particularly, tetra, penta and hexa phosphate analogs, where the resulting products can be exploited to generate a greater amount of signal or more highly resolved signal, than that resulting from the cleavage of the phosphate group that releases a single pyrophosphate molecule.

One readily available application for the methods and systems of the invention is in the area of nucleic acid sequence determination, and particularly in the area of pyrosequencing. A number of other applications are similarly available for the invention and will be clear from the discussion, below.

II. Pyrosequencing

A. Generally

Pyrosequencing is one approach to sequencing by synthesis, which measures the release of pyrophosphate from an incorporated nucleotide triphosphate into a nascent nucleic acid strand. By providing only a single type of nucleotide at a time, and measuring release of pyrophosphate, if any, one can determine whether the added nucleotide was actually incorporated, and thus identify the complementary base in the template sequence. These pyrosequencing methods typically rely upon a reporter system that produces light in response to the presence of pyrophosphate (See, U.S. Pat. No. 6,210,891, the full disclosure of which is incorporated herein by reference in its entirety for all purposes). In particular, the reporter system includes an ATP sulfurylase, AMP and a chemiluminescent system that employs a luciferase enzyme. Pyrophosphate produced during an incorporation reaction is reacted with AMP, in a reaction mediated by the sulfurylase enzyme, to produce ATP. The ATP is, in turn, reacted with the luciferase enzyme to produce light. If pyrophosphate, and consequently, light, is produced when a particular base is added to the reaction, one can determine that the particular base was added in a template dependent polymer extension reaction, and thereby identify the complementary base in the template sequence. If no light is generated, one can surmise that the added base was not complementary to the template, and the steps are repeated with a different nucleotide.

Figure 1:
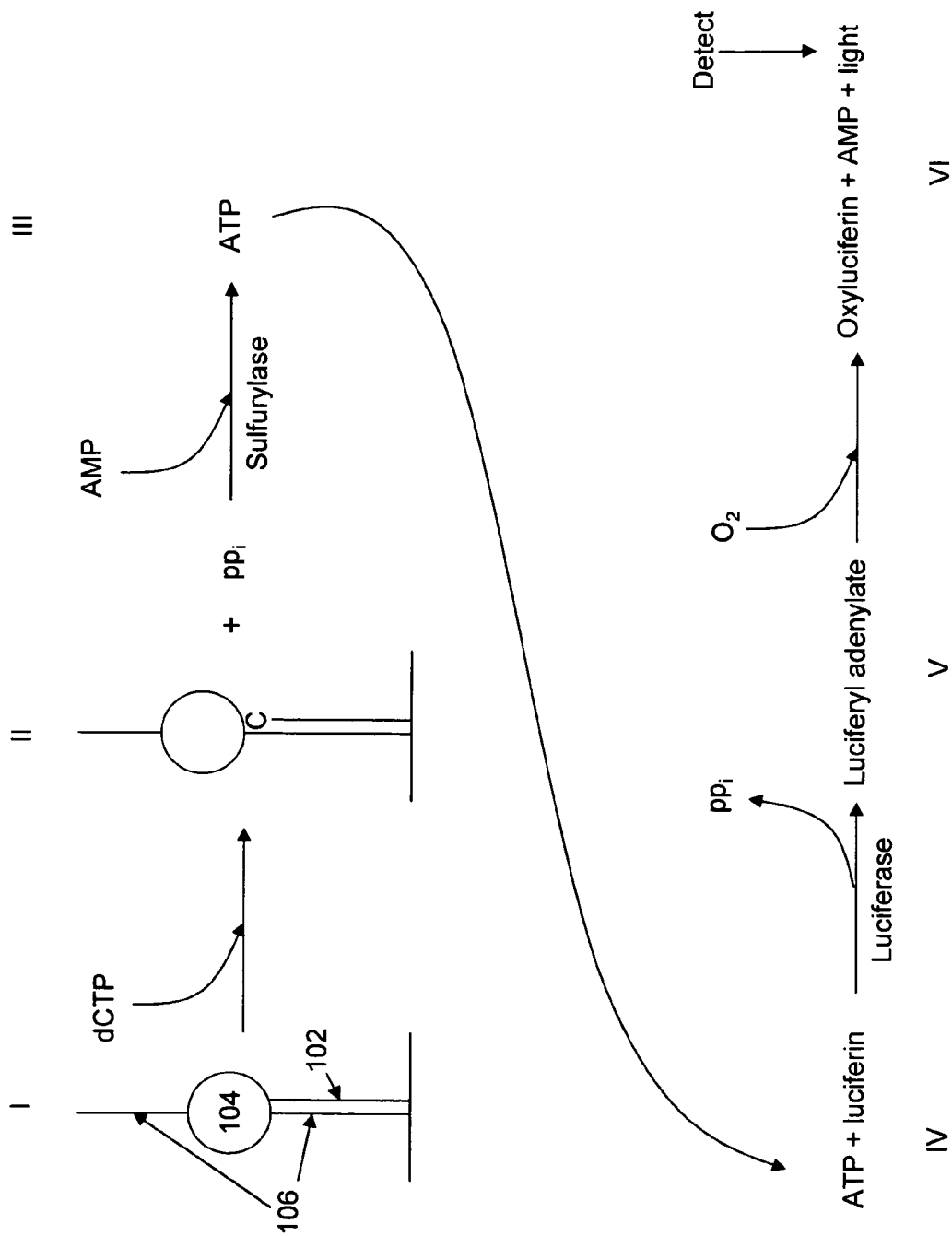
FIG. 1 provides a schematic illustration of a reaction scheme for monitoring polymerase incorporation of nucleotides using conventional pyrosequencing techniques.

A schematic illustration of an exemplary pyrosequencing system is provided in FIG. 1. As shown a template nucleic acid 100 is provided complexed with a primer sequence 102 and a DNA polymerase 104, and the complex is tethered to a solid support 106 (I). The support may be a particle or a surface of a larger substrate, e.g., a planar substrate. When the complex is contacted with a particular deoxynucleotide, e.g., dCTP as shown, it may be incorporated by the polymerase into the synthesizing, or 'nascent', strand if it is complementary to the template sequence. If it is not complementary to the next base in the template, it should be discarded by the polymerase without being incorporated. As shown, the base is incorporated (II). Upon incorporation, the polymerase mediated polymer extension reaction couples the nucleoside monophosphate (shown as "C") onto the 5' end of the nascent strand and releases pyrophosphate group. The pyrophosphate is then reacted with AMP in the presence of the sulfurylase enzyme to produce ATP (III). The ATP is then reacted with luciferin in the presence of luciferase (IV) to yield luciferyl adenylate and pyrophosphate (V). Combination of this compound with molecular oxygen then produces oxyluciferin, AMP and light, which may be readily detected using conventional luminescence detection systems. In many cases, to avoid any cross interference of a dATP base with the luciferase enzyme system, dATP analogs may be employed for the incorporation reaction, which analogs are processible as natural dATP by the polymerase enzyme, e.g., yielding a pyrophosphate group, but which are otherwise not processible by luciferase (See, U.S. Pat. No. 6,210,891, the full disclosure of which is incorporated herein by reference in its entirety for all purposes).

As noted, generation of light in response to exposure to a given nucleotide triphosphate in this enzyme system is thus indicative that the particular nucleotide was incorporated and was complementary to the next base in the template sequence. By sequentially adding different nucleotides to the tethered complex, with wash steps between each addition, one can test each subsequent base on the template sequence to determine which base is the next complementary base to be added. In particular, one would typically cycle through the four different bases, e.g., A, T, G, C, in sequential addition, interrogation and wash steps. This cycling through the four bases is then repeated until the desired sequence information was obtained or until the data deteriorated beyond utility.

While this system is effective in producing a detectable signal from the incorporation of nucleotides into nascent strands, it suffers from certain drawbacks, including, for example, a limited signal generation capacity. In particular, in a perfectly efficient system, each base molecule incorporated into a nascent strand would yield a single pyrophosphate molecule that would then yield a single ATP molecule. That single molecule of ATP would then produce the corresponding amount of signal from the Luciferase enzyme system. Of course, the overall system will not be perfectly efficient and each step in the reaction cascade will contribute losses to the overall signal yield from a given reaction. Further, where reaction concentrations are extremely low, e.g., in the sub-micromolar (μM) range, e.g., nM, pM, fM, or aM ranges, or even at single molecule levels, the amount of potential signal generation becomes increasingly difficult to detect. By way of example, in order to provide detectable signals for multiple cycles of pyrosequencing in commercially available systems, it is believed that pyrophosphate concentrations at the outset of the sequencing operation must be provided such that they are between 100 nM and 1 μM and decrease with each successive cycle, in order to provide meaningful signals over the desired number of cycles. To be able to reduce this concentration or expand the number of cycles that may be processed, would provide a number of benefits, and the methods of the invention accomplish this.

In addition to the foregoing, additional problems can afflict pyrosequencing and other sequencing by synthesis methods that rely on the concurrent extension of populations of primers to provide sufficient signal generation, where such problems can impact the readlength, e.g., how many consecutive bases may be added and detected in a given analysis, as well as the integrity of data being derived from the reactions as more bases are incorporated. Briefly, several sequencing by synthesis methods, including pyrosequencing methods typically rely upon the concurrent base-wise extension of groups or populations of identical primer sequences using identical templates. Unfortunately, in each base addition cycle that should yield a base extension, e.g., the proper extending base is added to the complex, a subset of each population will not be properly extended with a correctly added base. For example, if the next base to be properly incorporated in a growing or nascent sequence is an A, most of the nascent strands will be extended by an added A. However, a fraction of the complexes in the population will not properly incorporate the A. In the ordered addition or cycling of bases in such sequencing methods, the failure to incorporate the A will not be remedied until such time as the next A cycle is reached, as the cycles will add the other three bases before adding an A again. As a result, these subsets of the population will lag behind the actual and proper incorporation of the rest of the population. This lagging incorporation, in addition to providing a reduction in correct incorporation signals, will also yield incorrect signal data, e.g., it will show incorporation at the next A cycle, whether the bulk of the population is extended by that A. This will result in an increasing level of signal noise resulting from such lagging syntheses.

Further, because each 'correct' base addition cycle, e.g., that would be expected to extend the nascent strand, will produce its own subset of unextended nascent strands, it will be appreciated that the problems associated with such lagging or "out of phase" syntheses will rapidly become problematic, yielding incorporation information that is too fraught with error to be useful. In particular, because the number of improperly unextended sequences will increase with increasing numbers of cycles, it will rapidly cause a deterioration of the data derived from later cycles and prevent accurate interpretation of signals derived from base incorporation. Similar de-phasing of the incorporation data occurs when synthesis gets ahead of the expected incorporation. In particular, where there is carry-over of other bases in subsequent cycles, e.g., that were insufficiently washed from a previous cycle, they can result in the extension of a nascent strand beyond that which proper cycle based extension would be expected to yield. Accordingly, it would be desirable to provide such systems with a pressure for such reactions to remain "in phase" or otherwise move back into phase. The invention provides methods for applying such pressures.

B. Improved Pyrosequencing

1. Unlabeled Polyphosphates

The present invention generally provides improved assay methods, systems, reagents and kits for monitoring reactions that typically utilize nucleoside triphosphates as substrates, such as pyrosequencing analyses. In particular, the invention is directed to the monitoring of activity of enzymes that are capable of generating pyrophosphate from a nucleoside triphosphate. Examples of such enzymes include, e.g., nucleic acid polymerase enzymes (such as DNA polymerases and RNA polymerases), reverse transcriptases, telomerases, terminal deoxynucleotidyl transferases, and the like. By "monitoring the activity of an enzyme" is meant that one can monitor a relative level of activity of a given enzyme, in both quantitative and non-quantitative fashions, including to the point of identifying the presence or absence of such enzyme in a system as well as potentially quantifying that presence. Additionally, monitoring the activity of an enzyme also encompasses utilizing an enzyme's activity, e.g., with respect to a given substrate or reactant system, to derive other information. For example, in preferred aspects, as noted elsewhere herein, one can monitor an ability of an enzyme to incorporate nucleotides into a nascent nucleic acid strand in a template dependent fashion, and as a result, derive information about the template nucleic acid, e.g., its nucleotide sequence, or the presence of variations in that sequence. A variety of other applications may be served by such monitoring, including the identification of substrates for given reaction systems, e.g., enzymes, or in identifying effectors of such enzyme systems, e.g., inhibitors, enhancers, or the like.

The present invention provides methods of performing such assays utilizing nucleoside polyphosphates as the substrate that have more than three phosphate groups. Such polyphosphates include, e.g., nucleoside tetraphosphates, pentaphosphates, hexaphosphates and the like, and analogs of these compounds. By utilizing reactants that produce larger phosphate containing products, e.g., triphosphates, tetraphosphates, pentaphosphates or the like, one can more readily detect the reaction product, through a number of different methods. For example, and with reference to traditional pyrosequencing methods, in particularly preferred aspects, one can potentially convert each polyphosphate product molecule into multiple molecules of ATP, as compared to conversion of a single pyrophosphate into up to a single ATP molecule in traditional pyrosequencing. In such systems where the production and detection of ATP is used to monitor the underlying reaction of interest, larger amounts of ATP produced from a single reaction would yield a consequently higher signal response from that single reaction, e.g., potentially approaching twice or three times the signal response as obtained from a comparable nucleoside triphosphate reagent. Such enhanced signals are achieved even without any added optically detectable labeling groups on the nucleoside polyphosphates, e.g., such compositions are preferably unlabeled.

Figure 2:
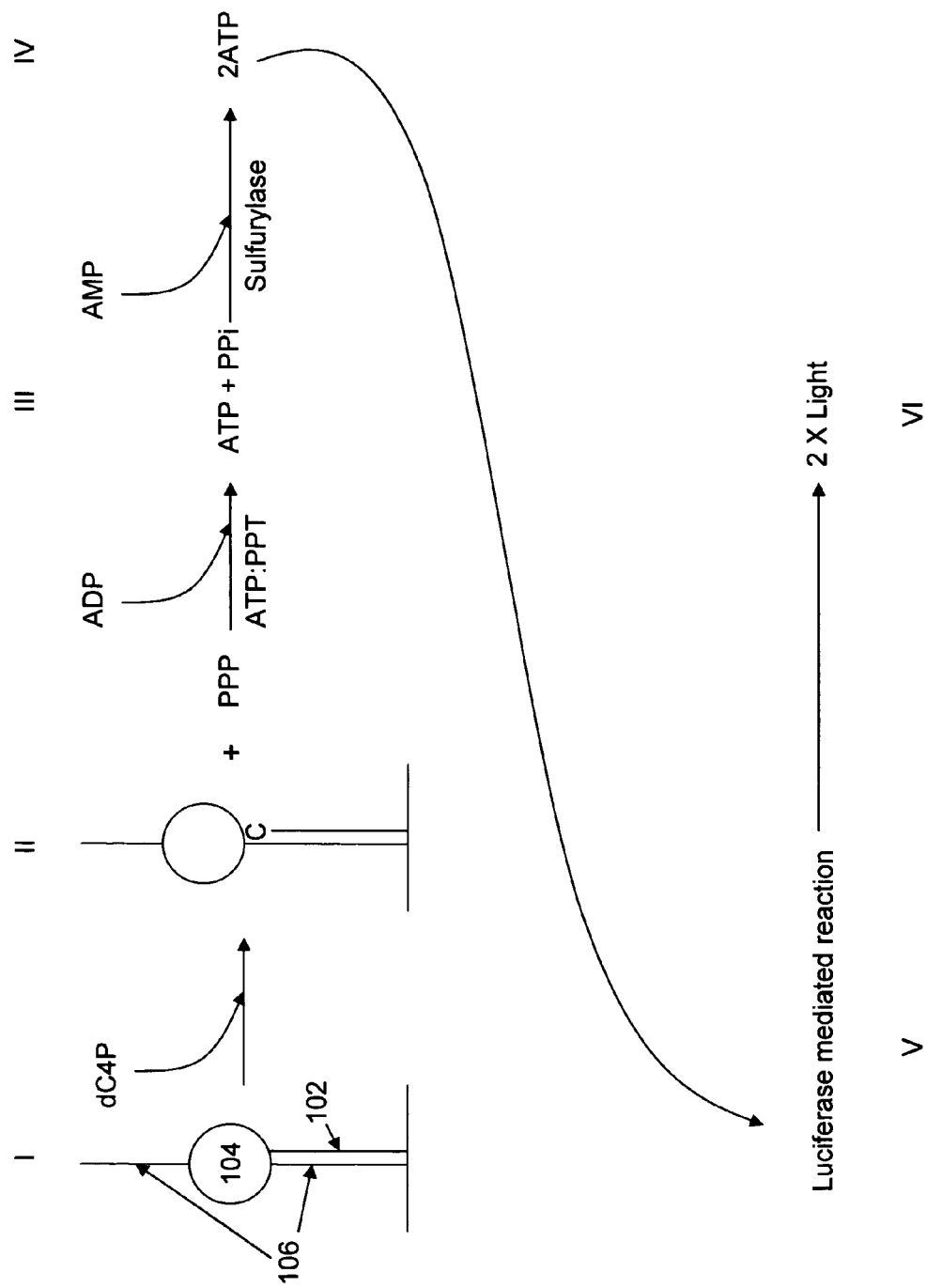
FIG. 2 provides a schematic illustration of the improved enzyme activity monitoring processes of the invention.

An exemplary reaction scheme employing a tetraphosphate analog, where the product is monitored using a luciferase enzyme system is shown in FIG. 2. As with the reaction set forth in FIG. 1, a template/primer/polymerase is provided (step I)(for ease of discussion, the same reference numerals are used as in FIG. 1). The complex is contacted with a nucleoside polyphosphate having more than three phosphate groups, e.g., a nucleoside tetraphosphate, as shown. Incorporation of the nucleoside tetraphosphate into the nascent strand by the polymerase then releases a triphosphate group (Step II), as opposed to a pyrophosphate as shown in FIG. 1. The triphosphate is then used to convert ADP into ATP, also yielding a pyrophosphate group (Step III). This reaction may be catalyzed by ATP:polyphosphate phosphotranferase (ATP:PPT), as shown. The pyrophosphate is then reacted with AMP to produce an additional ATP, in a sulfurylase catalyzed reaction (Step IV). As a result of this reaction, up to two ATP molecules could be generated from a single incorporation event. These two molecules are then subjected to the luciferase mediated reaction (Step V) to generate twice the amount of signal as compared to conventional pyrosequencing (Step VI). See, e.g., www (dot)genome.ad.jp/dbget-bin/www_bget?rn+r00136.

Although shown as a reaction of a triphosphate with ADP to create ATP and a pyrophosphate, followed by reaction of the resulting pyrophosphate with AMP, using ATP:PPT and sulfurylase catalyzed reactions, respectively, it will be appreciated that other enzymatic mechanisms could be used. In particular, other systems may be employed to generate more than one ATP molecule from each incorporation event. For example, the polyphosphate group, e.g., a triphosphate, could be reacted with AMP in a polyphosphate:AMP Phosphotransferase enzyme to yield ADP and pyrophosphate. The ADP is then further phosphorylated using an adenylate kinase enzyme and a free phosphate group. The remaining pyrophosphate group is then further used to produce an additional ATP molecule in a sulfurylase mediated reaction, as set forth above. See, e.g., Appl. Env. Microbiol. 66(5):2045-2051 (May 2000). The ATP produced is then detected and/or quantified using the same luciferase enzyme system of conventional pyrosequencing.

As set forth above, ATP detection is preferably carried out using chemiluminescent systems, and particularly a luciferase mediated system, as these systems are reported to be highly efficient. However, other ATP responsive reporter systems could be used to detect ATP. Such systems include, e.g., a reaction between 3-phosphoglycerate and ATP catalyzed by phosphoglycerate kinase. This reaction is coupled with a dephosphorylation reaction that involves the oxidation of NADH to NAD+, which is then quantitated by measuring the change in absorbance at 340 nm (See, e.g., Bucher, T. (1947) Über ein phosphatübertragendes Gärungsferment. Biochim. Biophys. Acta 1:292). Other ATP detection systems include, e.g., microsensor based systems as described in, e.g., Llaudet et al., *Anal. Chem.*, 77 (10), 3267-3273, 2005, and membrane based ATP gated ion channels for use as sensors, as described in Hazama et al., Arch. 1998, 437:31-35.

In addition to the foregoing, and as noted previously, additional polyphosphate analogs may also be used and generate a higher signal level per incorporation event than is the case with conventional pyrosequencing. For example, in some cases, one may use nucleoside penta- or hexaphosphates or their analogs. Incorporation of these analogs during nucleic acid synthesis then yields tetra or penta-phosphate groups that may be used as phosphate sources for generation of greater amounts of ATP, in vitro, using the above described enzymatic systems. In one particular example, the polyphosphate released upon incorporation is used to generate ADP from AMP in accordance with the equation $(P_i)_n + AMP \rightarrow ADP + (P_i)_{n-1}$. The ADP is then regenerated into AMP by the adenylate kinase system according to the equation: $2ADP \rightarrow AMP + ATP$.

This will go until pyrophosphate is reached analogous to above. As a result, one ATP is generated for every 2 phosphates from the polyphosphate, plus one from the terminal pyrophosphate. A potentially more elegant way to accomplish the same goal would use polyphosphate kinase, which creates ATP directly from polyphosphate: $(P_i)_n \rightarrow ATP + (P_i)_{n-1}$. This would generate one ATP per phosphate on the polyphosphate tail.

In any instance where a polyphosphate kinase may have activity on the nucleoside polyphosphate, such effects may be mitigated by employing a capping group on the terminal p0hossphate, thus enabling the kinase to only act upon the cleaved polyphosphate. A variety of capping groups may be employed on the terminal phosphate, including, e.g., capping groups well known in synthetic chemistry art.

The nucleoside polyphosphate compositions used in the context of the present invention, e.g., having greater than three phosphate groups, or analogs of such compounds, are generally characterized by having the following structure:

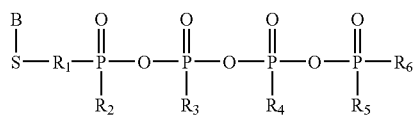

where B is a nucleobase selected from A, T, G and C bases;
S is a sugar moiety, and is typically deoxyribosyl;
$R_1$ is selected from O and S;
$R_2$-$R_5$ are independently selected from O, $BH_3$, and S; and
$R_6$ is selected from O,

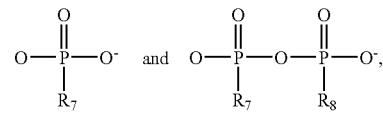

where $R_7$ and $R_8$ are independently selected from O, $BH_3$, and S.

Additional configurations of such nucleoside polyphosphates may be used, provided they operate as substrates for the enzyme of interest, e.g., a nucleic acid polymerase, and generate a polyphosphate product that is then susceptible to the enhanced detection methods, e.g., as described herein. Such additional configurations could also include much longer polyphosphate chains, e.g., where $R_6$ is $(PO_3)_n$ or analogous structures, e.g., as shown above, where n may be 3, 4, 5, 6, or greater, provided they are incorporatable or otherwise processable by the enzyme system of interest. Such compounds would be expected to yield even greater amounts of signaling capability due to the ability to produce greater amounts of ATP from such larger polyphosphate molecules. In addition to the variations in the polyphosphate component, it will be appreciated that any of a variety of incorporatable, non-naturally occurring nucleosides may be employed in the present invention, e.g., in addition to or as an alternative to one or more of A, T, G and C.

2. End Labeled Polyphosphates

While the foregoing improved methods and compositions are preferably carried out using unlabeled nucleoside polyphosphates, in another alternative aspect, labeling groups may be employed, where the release of the pyrophosphate (or other polyphosphate component) of an incorporated nucleoside polyphosphate may be detected using other systems that make up for additional shortfalls of the enzymatic/chemiluminescent systems of pyrosequencing. In particular, because signal generation in traditional pyrosequencing relies upon a two enzyme system (sulfurylase and luciferase), as well as apyrase for regeneration, background from the enzyme systems has been known to limit the lower detection limit of the assay, resulting in thresholds for minimum sample size. Consequently, it would be desirable to utilize a simpler signal generation system that could yield potentially higher sensitivity, and thus reduce sample size as well as reagent costs.

In accordance with this aspect of the invention, generation of the polyphosphate by-product of nucleotide incorporation is carried out, at least in part, via a label group coupled to the terminal phosphate group of the polyphosphate. The labels used typically yield a signal following their release in conjunction with the polyphosphate by-product that is differentially detectable from any signal produced by the labeled nucleoside polyphosphate, e.g., prior to incorporation. The use of end labeled nucleoside polyphosphates has been described in sequencing by synthesis and other analytical reactions. See, e.g., Published U.S. Patent Application No. 2003/0044781. Additional published applications purport to describe the use of such compounds and include, e.g., 2003/0162213, 2003/0124576, 2003/0077610, 2004/0224319, and 2004/0241716. The full disclosures of each of these publications is hereby incorporated herein by reference in its entirety for all purposes.

The present invention is directed to end-labeled nucleoside polyphosphates whose label undergoes a shift in its emitted or transmitted signal once it is released from the nucleoside polyphosphate during the incorporation reaction. Such shifts in signal include both shifts in signal intensity and signal characteristics, e.g., wavelength, as well as combinations of these.

Examples of such nucleoside polyphosphates include tri, tetra, penta, hexa or larger phosphates, that include labels on the terminal phosphate that are brightened upon phosphodiester cleavage, such as Bodipy-515, which would be expected to yield 20 fold increase in brightness of the cleaved polyphosphate product over the uncleaved nucleoside polyphosphate (See Korlach et al., Proc. Nat'l Acad. Sci. U.S.A., 2004, 101(9):2800-2805). Still other exemplary labeled nucleoside polyphosphates give rise to enhanced fluorescence following cleavage of the phosphodiester linkage between the alpha and beta phosphates during polymerization, or upon by separation of the label from the polyphosphate, e.g., using an additional enzyme system such as alkaline phosphatase, or the like. Such groups include, e.g., 7-Hydroxy-9H-(1,3-dichloro-9,9-dimethylacridin-2-one (DDAO), nicotinamide, aminonaphthalenesulfonate, 2'-(or-3')—O—(N-methylanthraniloyl)-groups, coumarin derivatives, e.g., 7-hydroxycoumarin and diethylaminocoumarin, fluorescein and rhodamine derivatives, e.g. fluorescein and tetramethylrhodamine, i 9H-(1,3-dichloro-9,9-dimethyl-7-hydroxyacridin-2-one) 9H-(9,9-dimethyl-7-hydroxyacridin-2-one) 9H-(1,3-dibromo-9,9-dimethyl-7-hydroxyacridin-2-one) 1I Resorufin Umbelliferone (7-hydroxycoumarin) 4-Methylumbelliferone 4-Trifluoromethylumbelliferone I3-Cyanoumbelliferone 3-Phenylumbelliferone 3,4-Dimethylumbelliferone 3-Acetylumbelliferone I16-Methoxyumbelliferone 111|SNAFL Fluorescein-alkyl ether Naphthofluorescein 11 Naphthofluorescein alkyl ether SNARFTM Rhodol green meso-Hydroxymonocarbocyanine meso-Hydroxytricarbocyanine meso-Hydroxydicarbocyanine bis-(1,3-dibutylbarbituric acid) pentamethine 111 Oxonol 111-Ethyl-2-(naphthyl-1-vinylene)-3,3-dimethyl-4-(3H)-6-indolinium salt 2-Hydroxy-5'-chloro-phenyl-chloro-quinazolone Trifluoroacetyl-R110 Acetyl-R110 8-Hydroxy-2H-dibenz (b, f) azepin-2-one 8-hydroxy-11,11-dimethyl-111H-dibenz (b, e) (1,4) oxazepin-2-one Hydroxypyrene 2-hydroxy-11,11-dimethyl-11H-dibenz (b, e) (1,4) oxazepin-8-one, among others.

In other examples, labeled nucleoside polyphosphates may be employed that yield shifts in signal wavelengths upon cleavage of the polyphosphate from the nucleoside polyphosphate, again followed by separation of the label from the polyphosphate component. Such compounds include, e.g., DDAO. A number of these dyes are commercially available from, e.g., Invitrogen/Molecular Probes (Eugene Oreg.) and are generally described in the Molecular Probes Handbook at probes.invitrogen.com/ handbook/. A wide variety of different labels are additionally described in Published International Patent Application No. WO 2004/072304, the full disclosure of which is hereby incorporated herein by reference. Other labeling compounds may be used that become fluorogenic upon phosphodiester cleavage and subsequent removal of the polyphosphate group, or that have enhanced uncaging upon phosphodiester cleavage and optional polyphosphate removal.

3. Phase Sweeping

As noted previously, a number of sequencing by synthesis methods suffer from a de-phasing problem that prohibits such methods from being used for extended read-lengths. The present invention provides methods that would be expected to provide pressure for lagging syntheses to catch up with the bulk of the populations of syntheses. In at least a first aspect, the invention provides for a change in the order of base addition in each cycle following an initial set of base additions.

Restated, in a pyrosequencing or other sequencing by synthesis method that employs repeated cycles of adding individual different bases to a sequencing complex, a first set of base addition steps are carried out in which the bases are added in a first order, e.g., A, then T, then G, and then C. After a number of cycles in the first set of additions, the order of base addition is changed to a second order, different from the first order, in a second set of base addition steps.

In preferred aspects, the second order of base addition is determined at least partially based upon the sequence information obtained from the first set of base additions. In particular, by matching base additions to an immediately preceding sequence of incorporated bases, as determined in the first set of base additions, one can pressure or "sweep" any lagging syntheses to catch up with the bulk of the remaining syntheses. The number of base addition cycles, or the number of actually incorporated bases, e.g., determined base sequence, before changing the order of base additions can be varied to achieve the optimal pressure and sequence read-length. For example, the order may be altered after 3, 4, 5, 6, 8, 10 or more bases are incorporated into the nascent strands. Alternatively, the order may be altered after a set number of individual base addition cycles regardless of the rate of actual incorporation, such as after 4, 8, 10, 20, 50 or more individual base addition cycles. In addition to the foregoing, during any particular analytical operation, the order of base addition may be changed twice, three times, four times, five times, ten times or more (e.g., to a third order, a fourth order, a fifth order, etc.), to accomplish a desired sequence determination.

By way of example, in a given analysis, a population of substantially identical tethered primer/template complexes is subjected to a number of base addition cycles where the bases were added in a set order, e.g., repeating cycles of A, G, T, then C. Following the number of base addition cycles using a first base addition order, four distinct bases are known to have been incorporated in a first sequence of incorporation, e.g., A, T, T then A. In order to sweep any lagging syntheses, the order of base addition would be changed to A followed by T (which would incorporate twice as a result of the repeated Ts), then A. This would be expected to cause most of the lagging sequences to catch up with those that have properly incorporated the bases. Because sequences may have repeated bases, e.g., two, three or more of a given base in a row, the second order of base additions will not always perfectly match the immediately preceding sequence, but it will generally match the order of base differences, e.g., the transition to a different base, in a sequence, e.g., for the incorporation sequence described above, the order of base differences is A, followed by T followed by A, as the transition from the first T to the second T does not constitute a transition to a different base.

With respect to carried over sequences, e.g., those that are incorporated faster than the bulk of the complexes in a reaction, one can apply a slight negative pressure to the overall synthesis to maintain coherent extension. In particular, by exposing the complexes to low levels of exonuclease activity, e.g., 3'-5' exonucleases. Briefly, such exonuclease activity would be expected to periodically cleave any overextended sequences, along with the terminal nucleotides on any properly extended sequences. Because the exonuclease activity is present only at low levels, it would result in only a slight backward pressure on the syntheses. When combined with the sweeping techniques and proper incorporation during ordinary synthesis provided above, however, the forward, in phase pressure would be expected to provide overwhelming compensation for the exonucleoase activity, resulting in an enhanced ability for such syntheses to remain in phase.

C. Other Sequencing Applications of Compositions

The polyphosphate analogs of the present invention are also usefully applied to other sequencing by synthesis processes that rely upon detection of by-products of the polymerase reaction, e.g., pyrophosphate, by means other than the chemiluminescent systems of traditional pyrosequencing. In particular, for systems that measure the level of free phosphate in the form of, e.g., pyrophosphate, the existence of a larger free phosphate chain, e.g., tri or tetra phosphate should give rise to greater detectability of the species. For example, where pyrophosphate is separated from unreacted nucleotides and detected electrophoretically, the greater charge level of a triphosphate or tetraphosphate relative to a pyrophosphate should make such separation more readily attainable.

Although described in considerable detail in terms of nucleic acid sequence determination using, e.g., Sequence by Synthesis techniques, it will be appreciated that the methods of the invention, even when applied to nucleic acid systems are not limited to the determination of strings of sequential bases in a oligo or polynucleotide. For example, such systems may be used to identify single bases within oligo or polynucleotides, such as in single nucleotide polymorphisms (SNPs), as well as other polymorphic variants, e.g., deletions, additions, substitutions, repeat sequences, or the like, in haplotyping assays, and the like.

In addition to the foregoing, the methods and compositions of the invention may be employed as a real-time indication of nucleic acid synthesis, e.g., similar to real-time PCR techniques, such as Taq-Man processes sold by Applera Corp. In particular, and with reference to polymerase chain reactions, amplification of nucleic acid sequences would typically result in increased or amplified levels of pyrophosphate within the reaction mixture. Detection of this product separated from the thermal cycling aspects of the operation using the enzyme systems described herein would provide a first alternative to the conventional systems. By further applying the nucleoside polyphosphate compositions of the present invention, one further increases the amount of signal resulting from such amplification by virtue of the generation of free polyphosphate that is, in turn, converted to multiple ATP molecules, giving rise to an amplified signal, again in a reaction separated from the thermal cycling processes of conventional PCR systems.

It will generally be appreciated that the methods of the invention are generally applicable to any analyses where nucleic acid synthesis or production is monitored, including in vivo studies, pharmaceutical screening applications, e.g., that target genetic replication, and the like.

III. Application of Improvements to Non-Sequencing Assay Systems

In an alternative application, the polyphosphate analogs described herein may provide further enhancements to other phosphate enzyme mediated reactions. For example, in reactions that rely upon a differential charge between a phosphate containing substrate and the product in which the phosphate is removed, the use of larger polyphosphate chains will give rise to greater charge shifts, and thus be more readily identifiable. For example, in electrophoretic processes where one is measuring the amount of phosphate removed from a nucleoside polyphosphate by separating labeled product, e.g., labeled nucleoside monophosphate, from substrate, e.g., labeled nucleoside triphosphate, a tetra or penta phosphate substrate would be expected to have a significantly more negative charge than the triphosphate counterpart. As such, it would be expected that a shift in electrophoretic mobility between substrate and product would be greater with the larger polyphosphate chain. A similar effect would be expected to be useful in other charge based phosphate analysis systems (see, e.g., U.S. Pat. No. 6,287,774, previously incorporated herein by reference).

IV. Kits and Systems of the Invention

The present invention provides for the overall systems described herein, as well as certain portions of the systems. The present invention also provides kits for carrying out the methods described herein. Typically, such kits include the nucleoside polyphosphates of the invention in conjunction with other requisite components of a given method. For example, in the case of luminescent assays, such kits will typically include the enzyme systems used to create ATP from the released polyphosphate, such as sulfurylase and ATP: PPT, as well as the luciferase enzyme system components. Such components may be packaged separately for mixing prior to performing the assay or they may be provided in other convenient formats, e.g., dried, frozen or otherwise packaged for efficient storage. Such kits will also typically include appropriate instructions for carrying out the methods of the invention, as set forth herein.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed:

1. A method of monitoring an activity of an enzyme that is capable of producing pyrophosphate from a nucleoside triphosphate, comprising:

contacting the enzyme with an unlabeled nucleoside polyphosphate having more than three phosphate groups; and detecting polyphosphate released from the nucleoside polyphosphate as an indicator of enzyme activity, wherein the step of detecting the polyphosphate comprises:

contacting the polyphosphate with an enzyme system capable of producing two or more ATP molecules from each polyphosphate molecule released; and detecting the ATP produced.

2. The method of claim 1, wherein the enzyme comprises a nucleic acid polymerase.

3. The method of claim 1, wherein the enzyme system in the detecting step comprises an ATP: Polyphosphate phosphotransferase enzyme, ADP and a sulfurylase enzyme.

4. The method of claim 1, wherein the enzyme system in the detecting step comprises a luciferase enzyme.

5. The method of claim 1, wherein the step of detecting ATP comprises contacting the ATP with a reporter system that is responsive to ATP.

6. The method of claim 5, wherein the reporter system comprises a luciferase enzyme reporter system.

7. The method of claim 1, wherein the nucleoside polyphosphate is selected from a nucleoside tetraphosphate, a nucleoside pentaphosphate, a nucleoside hexaphosphate or an analog thereof.

8. A method of monitoring an activity of a polymerase enzyme, comprising:

contacting the polymerase enzyme with a nucleoside polyphosphate comprising more than three phosphate groups, wherein the polymerase releases a polyphosphate group having at least three phosphates;

converting the polyphosphate group into at least two ATP molecules for each polyphosphate group released; and detecting an amount of ATP produced in the converting step as an indication of an activity of the polymerase enzyme.

9. A method of monitoring an activity of an enzyme system that is capable of releasing pyrophosphate from a nucleoside triphosphate, comprising:

contacting the enzyme system with a nucleoside polyphosphate having more than three phosphate groups, and contacting polyphosphate released from the nucleoside polyphosphate with an enzyme system capable of producing two or more ATP molecules from each polyphosphate molecule; and detecting ATP produced.

* * * * *